(12) United States Patent
Kitch et al.

(10) Patent No.: US 8,556,896 B2
(45) Date of Patent: Oct. 15, 2013

(54) DISTAL RELIEF FOR A SURGICAL DEVICE

(75) Inventors: Steven C. Kitch, Akron, IN (US); Tony L. Koser, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 674 days.

(21) Appl. No.: 12/694,776

(22) Filed: Jan. 27, 2010

(65) Prior Publication Data

US 2011/0184417 A1   Jul. 28, 2011

(51) Int. Cl.
*A61B 17/00* (2006.01)

(52) U.S. Cl.
USPC .................................................. 606/80

(58) Field of Classification Search
USPC ............ 604/164.13; 600/585; 606/60, 62–68, 606/80
See application file for complete search history.

(56) References Cited

U.S. PATENT DOCUMENTS

| | | | |
|---|---|---|---|
| 3,892,233 A | 7/1975 | Vestby | |
| 4,552,554 A * | 11/1985 | Gould et al. | 604/506 |
| 4,628,920 A | 12/1986 | Mathys, Jr. et al. | |
| 4,913,137 A | 4/1990 | Azer et al. | |
| 5,034,013 A | 7/1991 | Kyle et al. | |
| 5,100,404 A | 3/1992 | Hayes | |
| 5,364,393 A * | 11/1994 | Auth et al. | 606/34 |
| 5,624,446 A | 4/1997 | Harryman, II | |
| 5,855,579 A | 1/1999 | James et al. | |
| 5,968,048 A | 10/1999 | Harder | |
| 6,123,708 A | 9/2000 | Kilpela et al. | |
| 6,296,645 B1 | 10/2001 | Hover et al. | |
| 6,592,531 B2 * | 7/2003 | Bonutti | 600/585 |
| 6,702,823 B2 | 3/2004 | Iaia | |
| 6,709,436 B1 | 3/2004 | Hover et al. | |
| 6,808,527 B2 | 10/2004 | Lower et al. | |
| 7,232,442 B2 | 6/2007 | Sohngen et al. | |
| 7,527,627 B2 | 5/2009 | Ferrante et al. | |
| D611,225 S | 3/2010 | Khalil et al. | |
| 7,670,340 B2 | 3/2010 | Brivio et al. | |
| 7,771,428 B2 | 8/2010 | Siravo et al. | |
| 2002/0103488 A1 | 8/2002 | Lower et al. | |
| 2006/0015110 A1 | 1/2006 | Pepper | |
| 2006/0084999 A1 | 4/2006 | Aschmann | |
| 2006/0095039 A1 | 5/2006 | Mutchler | |
| 2007/0049940 A1 | 3/2007 | Wallace et al. | |

(Continued)

FOREIGN PATENT DOCUMENTS

WO   WO2009/143374 A2   11/2009

OTHER PUBLICATIONS

Zimmer Sirus Intramedullary Tibia Nail System—Surgical Technique, Anatomic Nail for Reamed and Nonreamed Technique, 06.00712.062—Rev 1 5MM, 2005.

(Continued)

*Primary Examiner* — Anu Ramana
(74) *Attorney, Agent, or Firm* — Schwegman, Lundberg & Woessner P.A.

(57) ABSTRACT

A distal tip wire relief section may be applied to any cannulated instrument or implant requiring the use of a guidewire with an enlarged head, such as a ball tip guidewire used in conjunction with an intramedullary nail. The implant incorporates an enlarged opening at the leading or distal portion of the cannula. The enlarged opening is selectively placed about the periphery of the distal portion to allow opening relief in areas where guidewire removal will be facilitated. Thus, a surgeon can reliably and repeatedly remove the guidewire after implantation of the implant by pulling the enlarged head of the guidewire proximally into and through the cannula.

21 Claims, 5 Drawing Sheets

(56) References Cited

U.S. PATENT DOCUMENTS

| | | |
|---|---|---|
| 2007/0265628 A1 | 11/2007 | Kraus et al. |
| 2007/0276385 A1 | 11/2007 | Schlienger et al. |
| 2008/0009869 A1 | 1/2008 | Schlienger et al. |
| 2008/0287949 A1 | 11/2008 | Keith et al. |
| 2009/0088752 A1 | 4/2009 | Metzinger et al. |
| 2009/0182278 A1 | 7/2009 | Eversull et al. |
| 2009/0306666 A1 | 12/2009 | Czartoski et al. |
| 2010/0094292 A1 | 4/2010 | Parrott |
| 2010/0174284 A1 | 7/2010 | Schwammberger et al. |

OTHER PUBLICATIONS

Zimmer Sirus INtramedullary Nail System—Brochure, Titanium nails with optimized anatomical designs for femoral and tibial fractures, 97-2290-001-00 5ML, 2005.

\* cited by examiner

FIG_5A

DISTAL RELIEF FOR A SURGICAL DEVICE

BACKGROUND

1. Technical Field

The present disclosure relates to cannulated surgical instruments. More particularly, the present disclosure relates to surgical instruments or implants used in conjunction with guidewires having enlarged heads, and to methods for using the same.

2. Brief Description of the Related Art

Rods or nails are used in a variety of surgical procedures, such as to treat fractures of long bones in the body. For example, an intramedullary (or "IM") rod or nail is a metal rod that can be inserted into the medullary cavity of a bone to bridge a fracture and aid in the healing process.

In one surgical technique used for intramedullary nail implantation, a guidewire with a spherical or ball tip is surgically introduced to the medullary cavity of a bone to bridge a fracture. A guidewire tube is then passed over the inserted ball tip guide wire. With the guidewire tube now bridging the fracture gap, the ball tip guidewire is removed from the tube and medullary cavity. A smooth guidewire is then inserted into the hollow guidewire tube, and the tube is removed to leave only the smooth guidewire in the medullary cavity of the bone. The smooth guidewire can then be used to guide an intramedullary nail into the medullary cavity by passing the cannula of the nail over the smooth wire as the nail is inserted. Once the nail is properly placed and secured, the smooth guidewire is removed through the nail cannula. This technique may be referred to as a "wire exchange" technique because the ball tip guidewire is exchanged for the smooth guidewire before insertion of the IM nail.

This wire exchange technique is typically performed because the size of the cannula in a traditional intramedullary nail is insufficient to allow passage of the enlarged head of a ball tip guidewire through the cannula. In a recent generation of intramedullary nails, however, improved designs and materials may allow for a larger nail cannulation which is sufficient to allow an enlarged head or ball tip of a guidewire to pass therethrough. Because the nail cannula is smaller than a typical guidewire tube, these recent designs may result in the ball tip becoming stuck or "hung up" when the shoulder between the ball tip and the wire shaft of the guidewire engages a lip or sharp edge of the distal terminus of the cannula.

To prevent the possibility of the ball tip guidewire becoming stuck as it is pulled proximally into the cannula, a surgeon may choose to perform a "wire exchange," thereby foregoing a savings in time that would result from using the ball tip guidewire as the guidewire for the intramedullary nail. Conversely, a surgeon attempting to save time in this manner may find that the ball tip of the guidewire becomes stuck at the distal end of the cannula.

What is needed is an intramedullary nail design in which a ball tip guidewire can be reliably used during the implantation of a surgical instrument, throughout the implantation procedure and without the need for a wire exchange.

SUMMARY

The present disclosure provides a distal tip wire relief section which may be applied to any cannulated instrument or implant requiring the use of a guidewire with an enlarged head, such as a ball tip guidewire used in conjunction with an intramedullary nail. The implant incorporates an enlarged opening at the leading or distal portion of the cannula. The enlarged opening is selectively placed about the periphery of the distal portion to allow opening relief in areas where guidewire removal will be facilitated. Thus, a surgeon can reliably and repeatedly remove the guidewire after implantation of the implant by pulling the enlarged head of the guidewire proximally into and through the cannula.

In one embodiment, a surgical device is used with a guide wire having an enlarged tip. The device includes an elongated body with an internal wall, a proximal end and a distal end, the elongated body defining a longitudinal cannula spanning the proximal end and the distal end. The internal wall defines an enlarged distal opening providing a distal access to the cannula, the enlarged distal opening having a maximum radial extent that is larger than the maximum radial extent of a corresponding proximate portion of the cannula. The internal wall also defines a continuous transition between the enlarged distal opening and the cannula, so that the opening is adapted to slidingly receive the enlarged tip of the guide wire.

In one aspect, the guide wire may have a ball tip with a maximum radial extent that is smaller than a maximum radial extent of the cannula. The guide wire may further include a wire shaft having a radial extent, so that a difference between the radial extents of the wire shaft and the ball tip is less than a difference between the radial extents of the ball tip and the cannula.

In another aspect, the surgical device may be a surgical implant, such as an intramedullary nail, for example. Alternatively, the surgical device may be a reamer.

In another aspect, the enlarged distal opening may be concave. The enlarged distal opening may also extend around less than the entirety of the periphery of the internal wall.

In yet another aspect, the elongated body may include a lead-in portion at the distal end, the lead-in portion defining an oblique angle with respect to a centerline of the elongated body.

In another embodiment, a method of placing a surgical instrument in a bone is provided and includes: guiding a guide wire with an enlarged distal tip along a path leading into a medullary cavity of a bone; providing a surgical instrument with a cannula and an enlarged relief portion at a distal end of the cannula, the distal relief portion having a radial extent that is larger than both of i) a maximum radial extent of the cannula proximate the distal relief portion and ii) a maximum radial extent of the enlarged tip of the guide wire; inserting the surgical instrument into the medullary cavity of the bone by guiding the cannula over the guide wire and moving the surgical instrument along the path of the guide wire; and, after the step of inserting the surgical instrument, removing the guide wire from the surgical instrument while the surgical instrument remains in the medullary cavity of the bone.

In one aspect, the step of providing the surgical device with a cannula and a relief portion includes providing a surgical device with a cannula and a concave relief portion.

In another aspect, a difference between the radial extents of the enlarged tip and the wire shaft of the guidewire is less than a difference between the radial extents of the enlarged tip and the cannula.

In another aspect, the step of providing a surgical device may include providing a surgical implant, such an intramedullary nail, for example. Alternatively, the step of providing a surgical device may include providing a reamer.

In yet another aspect, the enlarged distal opening extends around less than the entirety of the periphery of the internal wall of the surgical instrument at the distal end.

In another embodiment, an intramedullary nail for implantation within a bone is provided and includes a nail having a distal end, a proximal end, and a longitudinal centerline extending between the distal and the proximal end. An internal wall of the nail bounds a bore extending through the nail along the centerline, with the bore having a maximum transverse extent. A lead-in portion is disposed at the distal end of the nail, with the lead-in portion defining a distal face at an oblique angle with respect to the centerline, the distal face having an enlarged opening therein leading to the bore. The enlarged opening has a maximum transverse extent that is greater than the maximum transverse extent of the bore, so that the distal face defines a ramped guide surface and the enlarged opening provides a continuous transition between the internal wall and the distal face.

In one aspect, the opening in the distal face may be an ellipsoidal opening. The enlarged distal opening may also be concave. Further, the enlarged distal opening may extend around less than the entirety of the periphery of the internal wall.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figures 1, 3:
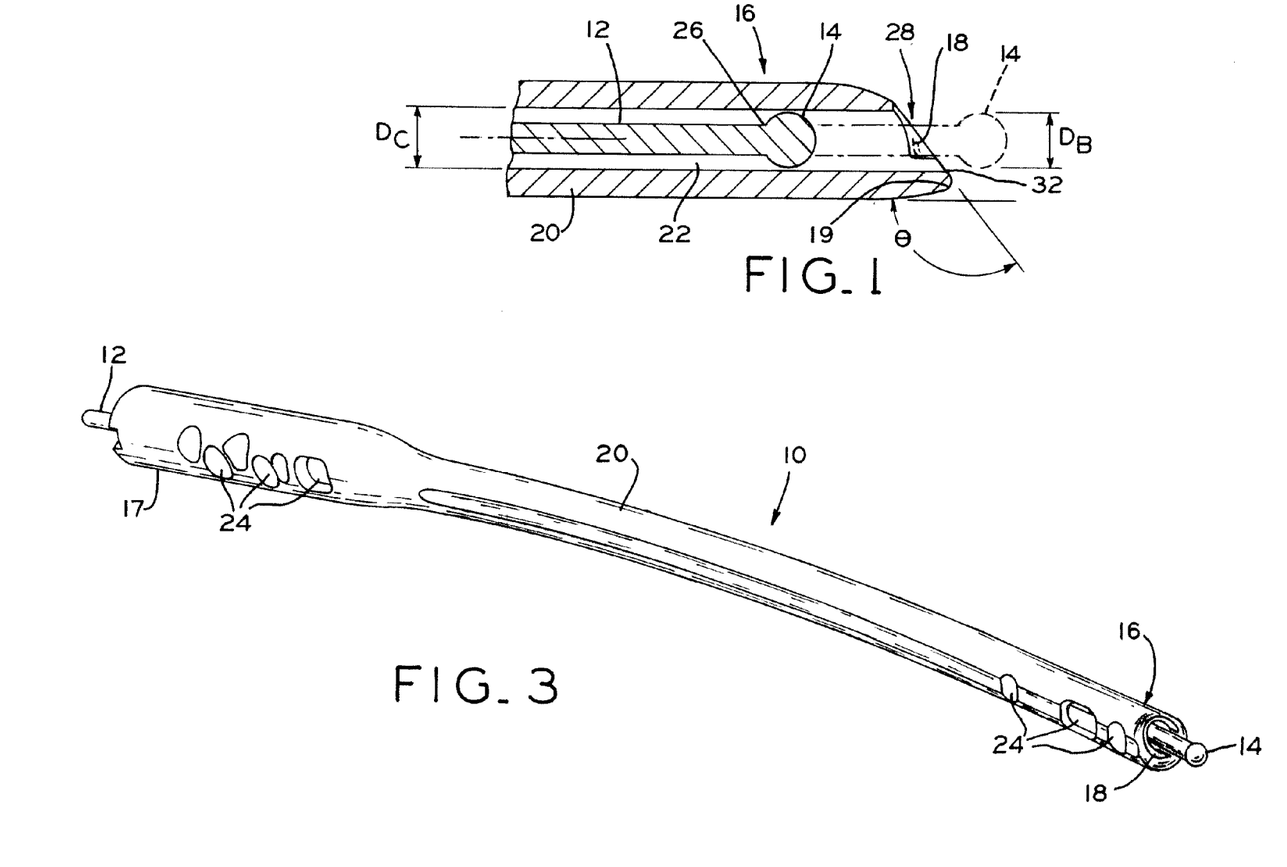
FIG. 1 is a partial section, elevation view of the distal tip of an intramedullary nail with a guidewire received therein, illustrating passage of a ball tip of a guidewire past a distal tip relief portion of the nail.
FIG. 3 is a perspective view of an intramedullary nail in accordance with the present disclosure, illustrating a ball tip guidewire extending therethrough.

Referring to FIG. 3, intramedullary nail 10 ("IM nail 10") has a cannula extending therethrough which receives guidewire 12 having ball tip 14 at a distal end thereof Distal portion 16 of IM nail 10 includes relief 18 adapted to facilitate guidance of ball tip 14 into the cannula of IM nail 10, as described in detail below. Although an intramedullary nail is used in the figures and description herein to illustrate a distal portion with a relief in accordance with the present disclosure, it is also contemplated that such a relief portion may be applied to any instrument or implant adapted for use with a guidewire having an enlarged tip or end portion. For example, other devices which may incorporate a distal relief portion in accordance with the present disclosure may include surgical tools such as reamer heads.

Figure 2A:
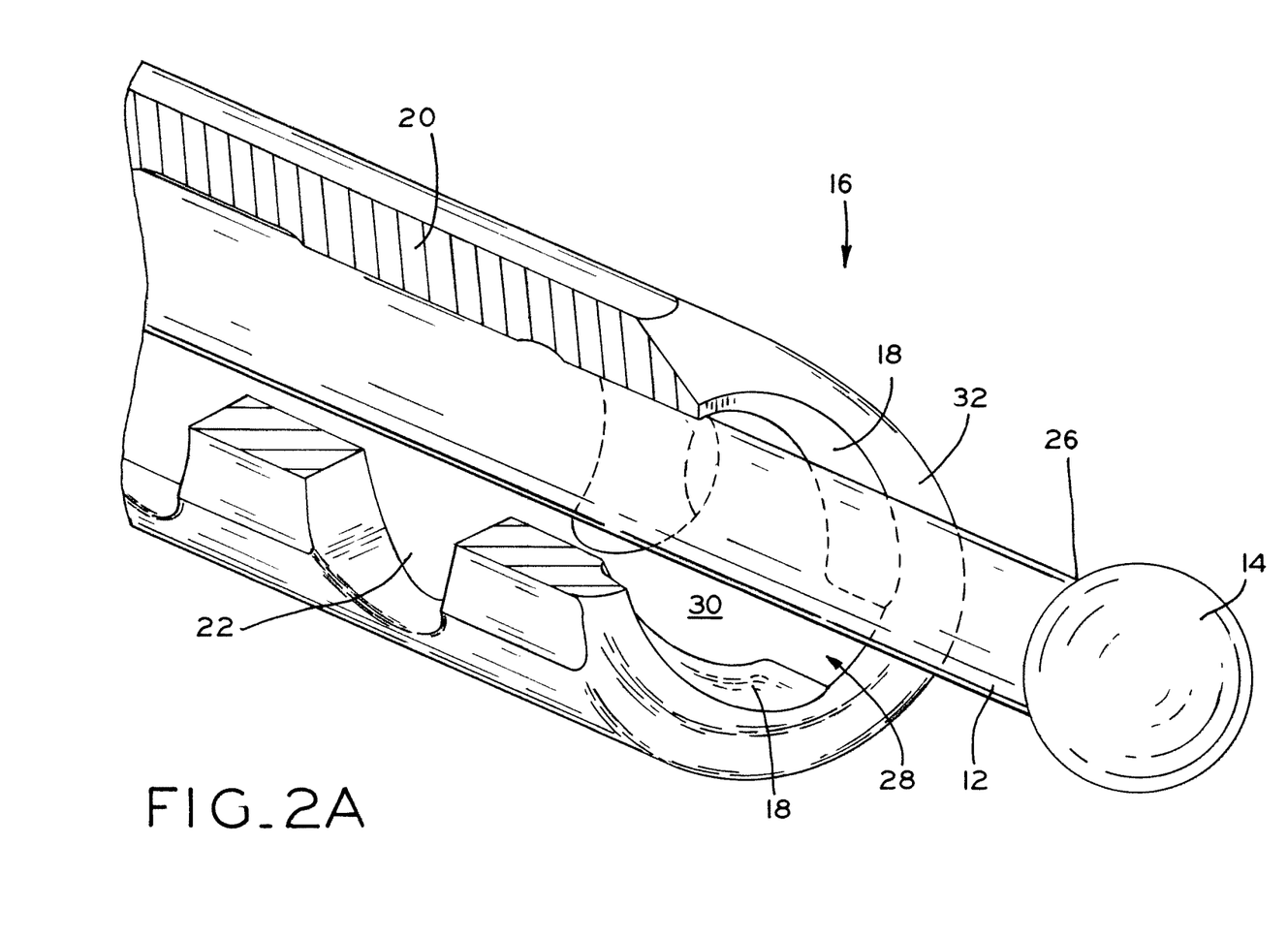
FIG. 2A is a perspective, partial section view of the distal tip relief portion of the intramedullary nail shown in FIG. 1, illustrating the ball tip extending past the distal tip of the nail.
Figure 2B:
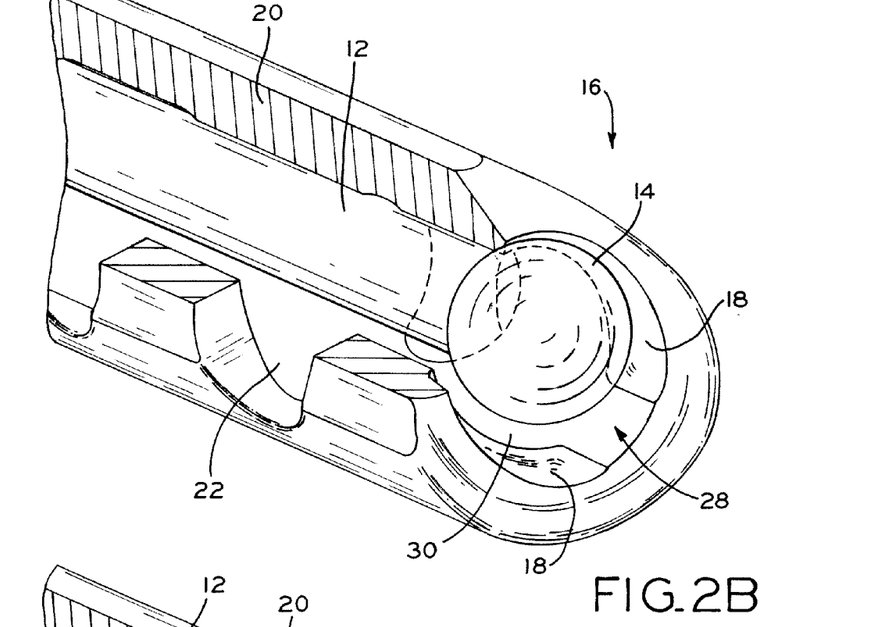
FIG. 2B is a perspective, partial section view of the intramedullary nail and guidewire of FIG. 2A, with the ball tip engaging the distal tip relief portion.
Figure 2C:
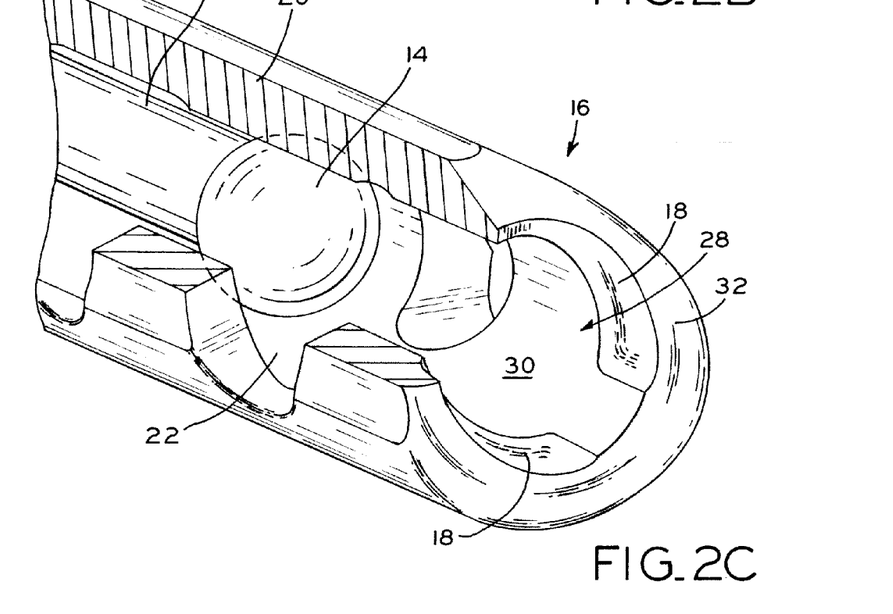
FIG. 2C is a perspective, partial section view of the intramedullary nail and guidewire of FIG. 2A, with the ball tip received within the nail cannula.

Referring generally to FIGS. 1-2C, IM nail 10 (FIG. 3) has elongated body 20 defining an axis or centerline and a bore or cannula 22 extending along the centerline. Cannula 22 extends along the entire length of IM nail 10 from proximal end 17 (FIG. 3) to distal end 16. As shown in FIG. 3, body 20 of IM nail 10 has curvature to conform with the natural curvature of a bone. Body 20 may further include a plurality of apertures 24 therethrough, such as for receiving screws or fasteners to affix IM nail 10 within the medullary canal of a bone.

Guidewire 12 has enlarged ball tip 14 at its distal end. Referring to FIG. 1, a shoulder or corner 26 may be formed between ball tip 14 and the main wire shaft of guidewire 12. Ball tip 14 has a diameter or maximum extent or dimension $D_B$ which is at least slightly smaller than the minimum transverse extent or dimension $D_C$ of cannula 22, to establish a clearance therebetween. For example, the clearance between a ball tip with a diameter of 3.0 mm and cannula 22 may be at least 0.008-in.

In the exemplary embodiment of FIGS. 1-2C, ball tip 14 is a generally spherically shaped structure received within a generally cylindrical cannula. However, the enlarged tip portion of the guidewire may be any shape or configuration, and the cannula may likewise take a variety of shapes or configurations as long as the radial extent of the enlarged tip portion is less than the radial extent of the cannula in at least one rotational configuration, so that the enlarged tip portion may pass through the entirety of cannula 22 from distal end 16 to proximal end 17.

As best seen in FIGS. 2A-2C, distal tip portion 16 of IM nail 10 includes distal tip relief 18 disposed at distal opening 28 and along inner wall 30. Relief 18 has a maximum transverse extent that is larger than the maximum transverse extent of the corresponding or adjacent proximate portion of cannula 22. A smooth transition is provided along relief 18 from distal surface 32 to the non-enlarged cannulated portion along inner surface 30, such as the concave profile shown in the illustrated embodiment. This concave profile, forming the smooth transition of relief 18, facilitates passage of ball tip 14 as it moves from outside of cannula 22 (FIG. 2A) to inside cannula 22 (FIG. 2C), as will be discussed in detail below.

In an exemplary embodiment, as best seen in FIGS. 2A-2C, relief 18 is created by sweeping a ball mill around a portion of inner surface 30 adjacent to distal surface 32. Thus, because the ball mill has a spherical radius, relief 18 is also radiused and has a generally concave profile. The ball mill may have a diameter which is larger than the diameter of cannula 22, so that relief 18 defines a concave surface with a radius of curvature larger than ball tip 14. The ball mill may also be smaller than the diameter of cannula 22 to impart a concavity of relief 18 with a radius equal to or smaller than ball tip 14. A smaller ball mill may also be moved along an arcuate path within distal opening 28, thereby milling an area with a complex or large-radius concavity. In one exemplary embodiment, the ball mill has a 0.188-in cutting diameter, and can be moved through a complex arcuate path to create relief 18 with a diameter larger than 0.188-in, such as by programming the complex arcuate path into a computer numerical controlled (CNC) machine.

Although relief 18 is shown extending only partially around the periphery of opening 28 in IM nail 10, it is within the scope of the present disclosure that relief 18 can vary according to the needs of a particular embodiment or surrounding geometrical configuration.

Referring again to FIG. 1, distal portion 16 of IM nail 10 defines a lead-in portion that is angled with respect to the centerline or axis of IM nail 10. More particularly, distal surface 32 defines a ramped surface created by cutting distal portion 16 at an oblique angle θ. The angled or ramped distal surface 32 facilitates passage of IM nail 10 into the medullary cavity of a bone by creating a relatively sharp "point" 19 at distal portion 16 (FIG. 1). Surface 32 also helps to guide ball tip 14 of guidewire 12 into relief 18 of IM nail 10. In the illustrated embodiment, the bottom portion of opening 28 is shown as not having been subjected to material removal so that relief 18 does not extend entirely around the periphery of opening 28. The angled profile of distal surface 32, i.e. the lead-in, precludes the need for relief 18 at this bottom surface. Further, because IM nail 10 is curved downwardly (FIG. 3), ball tip 14 of guidewire 12 is urged generally upwardly with respect to the perspective of FIGS. 1-2C, thereby minimizing the potential for contact or "hanging up" of corner 26 against the non-enlarged portion of opening 28. However, in other configurations, such as a straight IM nail or and IM nail with a non-angled distal surface 32, relief 18 may extend entirely around the periphery of opening 28.

Figure 5A:
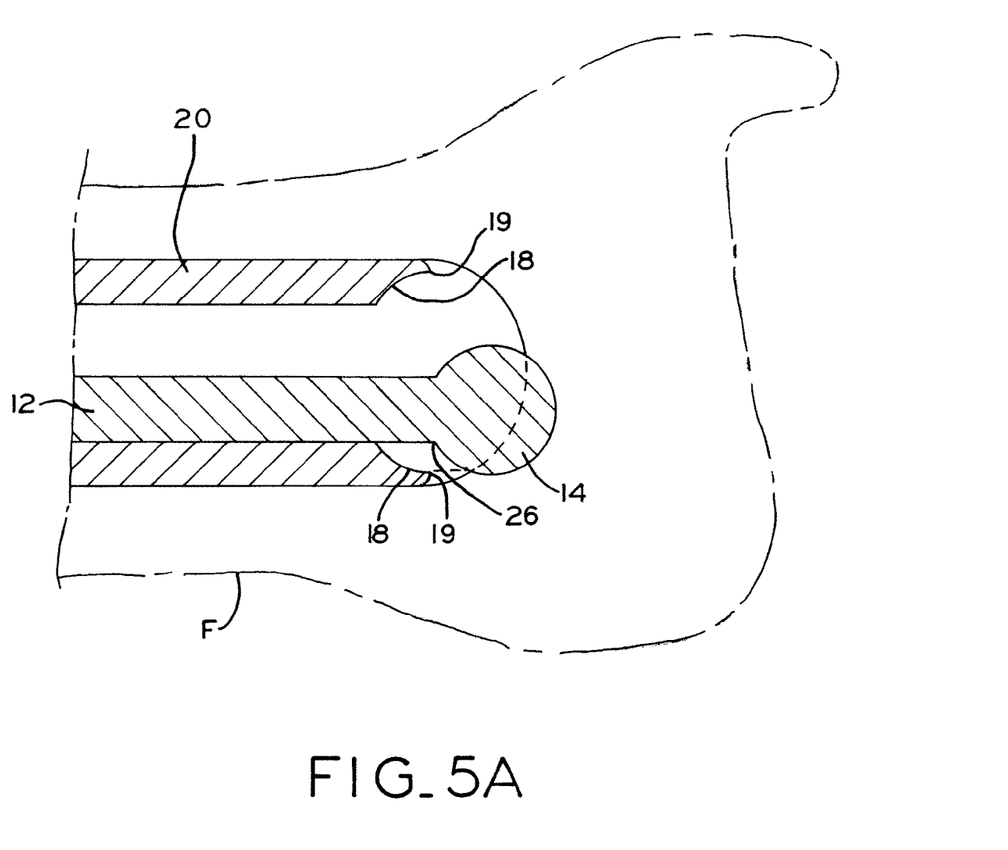
FIG. 5A is a detail, partial section view of a distal portion of the tibia shown in FIG. 5, illustrating the guidewire and distal tip relief.

When guidewire 12 is disposed within cannula 22 and ball tip 14 is extended beyond opening 28 (FIG. 2A), guidewire 12 may be pulled proximally so that ball tip 14 moves towards opening 28. As the wire moves proximally, ball tip 14 reaches opening 28 (FIG. 2B) and may contact relief 18. Because relief 18 defines a maximum transverse extent which is larger than the maximum transverse extent of cannula 22, corner 26 (formed between ball tip 14 and the main wire shaft of guidewire 12, as discussed above) cannot become lodged or engaged or hung up at the junction between inner surface 30 and distal surface 32 (FIG. 2C). In an exemplary embodiment, and as shown in FIG. 5A, the opening of relief 18 is sufficiently enlarged to ensure that the shaft of guidewire 12 will contact inner wall 30 before corner 26 can become stuck at edge 19 of relief 18. That is to say, if relief 18 is sufficiently large, edge 19 of relief 18 will contact the surface of ball tip 14 rather than corner 26, even when the shaft of guidewire 12 is moved transversely so as to contact inner wall 30. Corner 26 is therefore precluded from engaging a sharp lip or corner of distal surface 32 (FIG. 2C) so that ball tip 14 will not become "hung up" on relief 18. Therefore, ball tip 14 will reliably pass into relief 18, and the smooth transition between distal surface 32 and inner surface 30 of cannula 22 will then ensure that ball tip 14 passes from relief 18 into cannula 22. Once ball tip 14 has moved past relief 18, as shown in FIG. 2C, guidewire 12 may be pulled proximally through the remainder of cannula 22 and out of IM nail 10.

Figures 4, 5, 6:
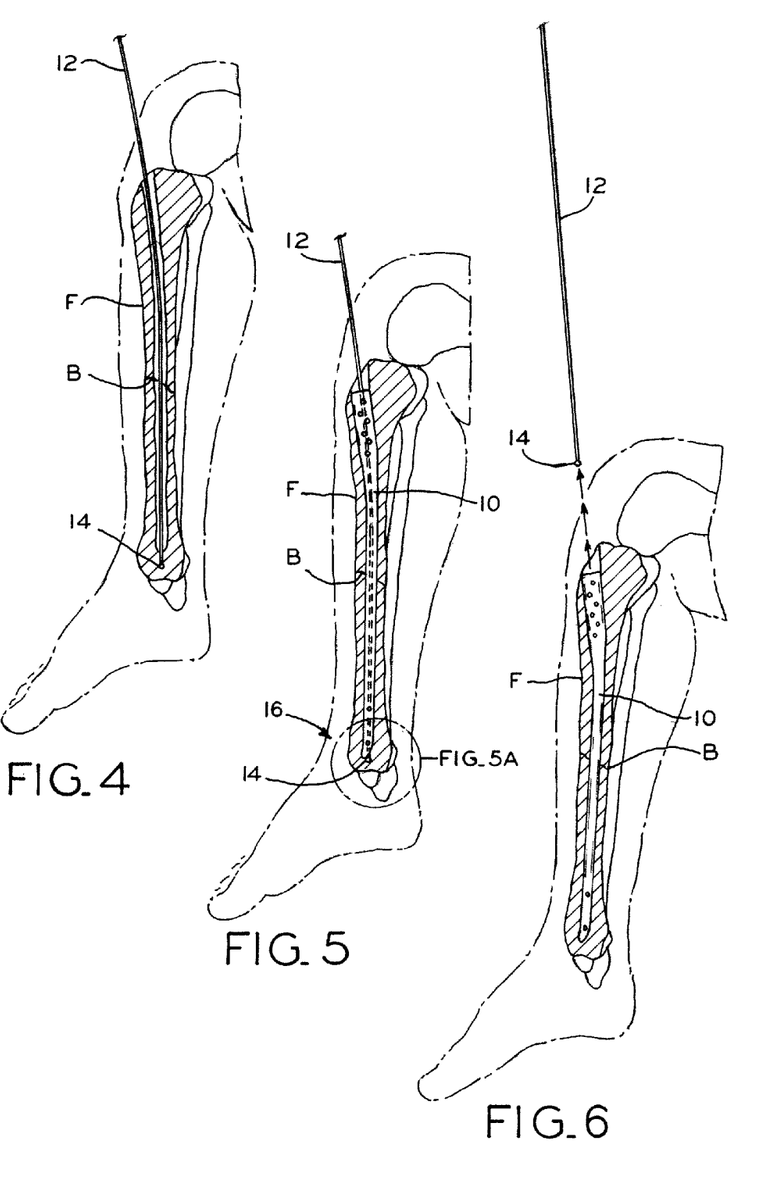
FIG. 4 is an elevation, section view of a tibia with a guidewire received within the tibial medullary canal.
FIG. 5 is an elevation, section view of the tibia of FIG. 4 with an intramedullary nail received within the medullary canal and over the guidewire.
FIG. 6 is an elevation, section view of the tibia of FIG. 4 with an intramedullary nail received within the medullary canal and the guidewire removed.

Referring now to FIGS. 4-6, an exemplary surgical procedure includes passing ball tip guidewire 12 into the medullary canal of a fractured femur F, such that guidewire 12 spans fracture B. With guidewire 12 fully inserted into the femur F (as shown in FIG. 4), IM nail 10 may be inserted into the medullary canal using guidewire 12 as a guide. Once IM nail is fully inserted (FIG. 5), guide wire 12 may be removed through cannula 22 of IM nail 10. As discussed above and shown in FIG. 5A, relief 18 ensures that ball tip 14 of guidewire 12 will not become stuck at edge 19 of distal end 16.

Advantageously, an intramedullary nail or other surgical instrument or implant may be used throughout a surgical procedure without the need for a "wire exchange." A surgeon can pass a guidewire with an enlarged head, such as guidewire 12 with ball tip 14, into a medullary canal to span a fracture gap. Rather than passing a temporary tube over the enlarged-head guidewire, removing the enlarged-head guidewire, and then inserting a smooth guidewire in its place, the enlarged-head guidewire may be left in place and the surgical implant installed directly over the guidewire without concern that the enlarged head of the guidewire will become stuck outside the distal end of the cannula.

Also advantageously, a surgical instrument with an enlarged distal opening in accordance with the present embodiment may be used without a wire exchange, even where the instrument has a relatively small cannulation size. Using IM nail 10 as an example and referring to FIG. 1, relief 18 prevents ball tip 14 from becoming stuck at distal surface 32, allowing the transverse extent $D_C$ of cannula 22 to be only slightly larger than the size of the transverse extent $D_B$ of ball tip 14. Thus, only minimal clearance between ball tip 14 and cannula 22 is required, allowing instrument designers to maximize the thickness of body 20. An instrument or implant made in accordance with the present disclosure therefore retains maximum implant or instrument strength while also eliminating the need to do a wire exchange during surgical implementation. For example, in one exemplary embodiment a cannulation size for an IM nail may be just over 3.0 mm in diameter (such as 3.008-in, as described above), while still allowing a guidewire with a 3.0 mm diameter ball tip to pass therethrough.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical system comprising:
 a guide wire having an enlarged tip;
 a surgical device with an elongated body, the elongated body comprising:
  an internal wall;
  a proximal end;
  a distal end, said elongated body defining a cannula spanning said proximal end and said distal end; and
  an enlarged distal relief portion at the distal end defined by the internal wall, the enlarged distal relief portion being concave with respect to a longitudinal axis of the cannula, and the enlarged distal relief portion defining an enlarged distal opening providing a distal access to said cannula;
 said enlarged distal relief portion having a maximum radial extent in a cross-section perpendicular to a longitudinal axis that is larger than said maximum radial extent in a cross-section perpendicular to the longitudinal axis of a corresponding proximate portion of said cannula; and
 said internal wall defining a continuous transition between said enlarged distal opening and said cannula, wherein a thickness of a wall of said enlarged distal relief portion increases from a distal end of said enlarged distal relief portion to a proximal end of said enlarged distal relief portion, whereby said enlarged distal relief portion is adapted to slidingly receive said enlarged tip of said guide wire.

2. The surgical system of claim 1, wherein said guide wire comprises a ball tip having a maximum radial extent that is smaller than a maximum radial extent of said cannula.

3. The surgical system of claim 2, wherein said guide wire further comprises a wire shaft having a radial extent, wherein a difference between the radial extents of said wire shaft and said ball tip is less than a difference between the radial extents of said enlarged tip and said cannula.

4. The surgical system of claim 1, wherein the surgical device comprises a surgical implant.

5. The surgical system of claim 4, wherein the surgical device comprises an intramedullary nail.

6. The surgical system of claim 1, wherein the surgical device comprises a reamer.

7. The surgical system of claim 1, wherein said enlarged distal opening is concave.

8. The surgical system of claim 1, wherein said enlarged distal opening extends around less than the entirety of a periphery of said internal wall.

9. The surgical system of claim 1, wherein enlarged distal relief portion defines faces at an oblique angle with respect to a longitudinal axis of said elongated body.

10. A method of placing a surgical instrument in a bone, the method comprising:
    guiding a guide wire with an enlarged distal tip along a path leading into a medullary cavity of a bone, wherein said guide wire further comprises a wire shaft having a radial extent and a corner formed between said enlarged distal tip and said wire shaft;
    providing a surgical instrument with a cannula and an enlarged relief portion at a distal end of the cannula defined by an internal wall of the cannula, the enlarged relief portion having a radial extent that is larger than both of i) a maximum radial extent of the cannula proximate the enlarged relief portion and ii) a maximum radial extent of the enlarged tip of the guide wire, wherein the enlarged relief portion is concave, with respect to a longitudinal axis of said surgical instrument, and wherein a thickness of a wall of said enlarged relief portion increases from a distal end of said enlarged relief portion to a proximal end of said enlarged relief portion;
    inserting the surgical instrument into the medullary cavity of the bone by guiding the cannula over the guide wire and moving the surgical instrument along the path of the guide wire; and
    after the step of inserting the surgical instrument, removing the guide wire from the surgical instrument while the surgical instrument remains in the medullary cavity of the bone, wherein said enlarged relief portion is configured such that when said shaft of said guide wire contacts said internal wall of said cannula, an edge of said enlarged relief portion contacts a surface of said enlarged distal tip and does not contact the corner.

11. The method of claim 10, wherein the step of providing the surgical device with a cannula and a relief portion comprises providing a surgical device with a cannula and a concave relief portion.

12. The method of claim 10, wherein a difference between the radial extents of the enlarged tip and the wire shaft is less than a difference between the radial extents of the enlarged tip and the cannula.

13. The method of claim 10, wherein the step of providing a surgical device comprises providing a surgical implant.

14. The method of claim 13, wherein the step of providing a surgical device comprises providing an intramedullary nail.

15. The method of claim 10, wherein the step of providing a surgical device comprises providing a reamer.

16. The method of claim 10, wherein the enlarged distal opening extends around less than the entire circumference of the internal wall of the surgical instrument at the distal end.

17. An intramedullary nail for implantation within a bone, the nail comprising:
    a nail having a distal end, a proximal end, and a longitudinal axis extending between said distal and said proximal end;
    an internal wall bounding a bore extending through said nail along said longitudinal axis, said bore having a maximum transverse extent;
    an enlarged relief portion disposed at said distal end, said an enlarged relief portion defining distal faces at an oblique angle with respect to said longitudinal axis, said distal faces defining an enlarged opening leading to said bore, said enlarged opening having a maximum transverse extent in a cross-section perpendicular to said longitudinal axis that is greater than said maximum transverse extent of said bore, whereby said distal face defines a ramped guide surface providing a continuous transition between said enlarged opening and said internal wall; and
    wherein said enlarged relief portion is concave, with respect to the longitudinal axis of said nail, such that a thickness of a wall of said enlarged relief portion increases from a distal end of said enlarged relief portion to a proximal end of said enlarged relief portion.

18. The intramedullary nail of claim 17, wherein said opening in said distal face comprises an ellipsoidal opening.

19. The intramedullary nail of claim 17, wherein said enlarged relief portion extends around less than the entire circumference of said internal wall.

20. The surgical system of claim 1, wherein said guide wire further comprises a wire shaft and a corner, the corner formed between said enlarged distal tip and said wire shaft, wherein said enlarged distal relief portion is configured such that when said wire shaft of said guide wire contacts said internal wall of said elongated body, the internal wall defining the enlarged distal relief portion contacts an external surface of said enlarged tip.

21. The intramedullary nail of claim 17, wherein said enlarged relief portion has a lead-in portion having a maximum diameter that is substantially the same as a maximum diameter of a portion of the intramedullary nail adjacent to the lead-in portion.

* * * * *